(12) United States Patent
Arnett

(10) Patent No.: US 11,660,407 B2
(45) Date of Patent: May 30, 2023

(54) NASAL DELIVERY DEVICE WITH SAFETY ROD

(71) Applicant: Eli Lilly and Company, Indianapolis, IN (US)

(72) Inventor: Jaime Ray Arnett, Fishers, IN (US)

(73) Assignee: Eli Lilly and Company, Indianapolis, IN (US)

(*) Notice: Subject to any disclaimer, the term of this patent is extended or adjusted under 35 U.S.C. 154(b) by 0 days.

(21) Appl. No.: 17/787,716

(22) PCT Filed: May 7, 2021

(86) PCT No.: PCT/US2021/031247
§ 371 (c)(1),
(2) Date: Jun. 21, 2022

(87) PCT Pub. No.: WO2021/231199
PCT Pub. Date: Nov. 18, 2021

(65) Prior Publication Data
US 2023/0024987 A1    Jan. 26, 2023

Related U.S. Application Data

(60) Provisional application No. 63/024,547, filed on May 14, 2020.

(51) Int. Cl.
*A61M 15/00* (2006.01)
*A61M 15/08* (2006.01)

(52) U.S. Cl.
CPC .... *A61M 15/0041* (2014.02); *A61M 15/0031* (2014.02); *A61M 15/0035* (2014.02);
(Continued)

(58) Field of Classification Search
CPC ............ A61M 15/003; A61M 15/0031; A61M 15/0035; A61M 15/0041; A61M 15/0061; A61M 15/08
See application file for complete search history.

(56) References Cited

U.S. PATENT DOCUMENTS

| 5,547,131 A | 8/1996 | Brace |
| 6,401,987 B1 | 6/2002 | Oechsel et al. |

(Continued)

FOREIGN PATENT DOCUMENTS

| WO | WO-2009090245 A1 * | 7/2009 | .......... A61M 15/007 |
| WO | 2019016408 | 1/2019 | |

(Continued)

OTHER PUBLICATIONS

Consort Medical, Nasal Spray Devices, Nov. 13, 2019.
(Continued)

*Primary Examiner* — Kathryn E Ditmer
(74) *Attorney, Agent, or Firm* — M. Daniel Spillman

(57) ABSTRACT

The present disclosure provides a nasal delivery device with a device body that includes a trigger end and an outlet end. The nasal delivery device also includes a trigger assembly coupled to the trigger end of the device body, a drug container supported by the device body, and a spring-loaded activator assembly supported by the device body and disposed between the trigger assembly and the drug container.

9 Claims, 6 Drawing Sheets

(52) U.S. Cl.
CPC ........ *A61M 15/0061* (2014.02); *A61M 15/08* (2013.01); *A61M 2202/064* (2013.01); *A61M 2205/8281* (2013.01)

(56) References Cited

U.S. PATENT DOCUMENTS

| | | | |
|---|---|---|---|
| 6,644,309 | B2 | 11/2003 | Casper et al. |
| 6,708,846 | B1 | 3/2004 | Fuchs et al. |
| 7,784,460 | B2 | 8/2010 | Djupesland et al. |
| 8,022,082 | B2 | 9/2011 | Zierenberg |
| 8,261,737 | B2 | 9/2012 | Von Schuckmann |
| 8,590,750 | B2 | 11/2013 | Warby et al. |
| 8,678,243 | B2 | 3/2014 | Collins et al. |
| 8,926,558 | B2 | 1/2015 | Ratjen et al. |
| 9,067,034 | B2 | 6/2015 | Djupesland et al. |
| 9,821,127 | B2 | 11/2017 | Barber et al. |
| 10,272,213 | B2 | 4/2019 | Allsop |
| 10,406,302 | B2 | 9/2019 | Andrade et al. |
| 2004/0153033 | A1* | 8/2004 | Mazzoni ............. B05B 11/0027 604/232 |
| 2006/0016833 | A1* | 1/2006 | Greiner-Perth ..... B05B 11/3056 222/383.1 |
| 2008/0210228 | A1 | 9/2008 | Corbacho |
| 2008/0210229 | A1 | 9/2008 | Corbacho |
| 2010/0095957 | A1 | 4/2010 | Corbacho |
| 2014/0231457 | A1* | 8/2014 | Allsop ................. A61M 15/08 222/153.13 |
| 2020/0316627 | A1* | 10/2020 | Poullain ................ B05B 12/002 |

FOREIGN PATENT DOCUMENTS

| | | |
|---|---|---|
| WO | 2019211424 | 11/2019 |
| WO | 2020154182 | 7/2020 |

OTHER PUBLICATIONS

ON drugDELIVERY, , "Pulmonary & Nasal Delivery", Issue No. 96, Apr. 11, 2019.

Marx, D., et al., "Intranasal Drug Administration—An Attractive Delivery Route for Some Drugs," Drug Discovery and Development—From Molecules to Medicine, Chapter 13, http://dx.doi.org/10.5772/59468.

Patent Cooperation Treaty Written Opinion of the International Searching Authority pertaining to International Application No. PCT/US2021/031247; International Filing Date: May 7, 2021; dated Oct. 14, 2021.

Patent Cooperation Treaty International Search Report pertaining to International Application No. PCT/US2021/031247; International Filing Date: May 7, 2021; dated Oct. 14, 2021.

* cited by examiner

NASAL DELIVERY DEVICE WITH SAFETY ROD

FIELD OF THE DISCLOSURE

The present disclosure relates to a nasal delivery device for containing a medicament, especially systemic or topical pharmaceuticals, or a vaccine to the nasal airway of a subject.

BACKGROUND

Diabetes has reached epidemic proportions in much of the western world and is a serious and growing public health concern in many developing economies. Globally, there are approximately 285 million people with diabetes and that number is expected to reach 438 million by 2030 (IDF Diabetes Atlas, 2009.)

Diabetes complications are usually associated with chronically elevated blood glucose levels (hyperglycemia), which result in heart, kidney and eye diseases, amputations and neurological impairment. Unfortunately, medications (e.g., insulin) used to treat diabetes-related hyperglycemia to reduce blood sugar levels often cause the patient's blood sugar level to drop too low and lead to hypoglycemia (low blood sugar).

Depending on the severity of the episode, hypoglycemia causes a wide range of physical problems ranging from weakness, dizziness, sweating, chills and hunger to more serious symptoms including blurred vision, behavior change, seizures, coma and even death. In addition to the physical effects of hypoglycemia, there are significant psychological effects including embarrassment, fear of another episode, high levels of anxiety and low levels of overall happiness that adversely affect glucose control and quality of life (Deary, 2008).

Glucagon is a highly effective treatment for severe hypoglycemia both outside and within the hospital setting. Historically, glucagon was available only as a powder that must be mixed with a diluent immediately prior to administration by injection. Although this is a procedure that would be relatively easy for people with diabetes who inject insulin, they are not treating themselves because, by definition, severe hypoglycemia is a hypoglycemic episode in which the patient requires third party assistance (Cryer, 2009). For any non-medical person who is confronted with an emergency situation in which a patient with diabetes is in a hypoglycemic coma or suffering hypoglycemia-related convulsions, reconstitution and injection of the current injectable glucagon is a complex and daunting procedure that is fraught with potential for errors.

Recently, the U.S. Food and Drug Administration (FDA) approved intranasal glucagon for the treatment of severe hypoglycemia. Compared to intramuscular glucagon that must be reconstituted and injected, intranasal glucagon may be ready-to-use in a single, fixed dose without requiring reconstitution or injection. The associated intranasal device is also easy to use and portable in case of emergency.

Nasal delivery devices are known for dispensing media such as powders and fluids for discharge into the body. Such device includes an actuator, an outlet nozzle, and a drug drive system that is activated by the actuator that causes the media to discharge from the outlet nozzle. There is a desire to continue to improve the sturdiness and measures to prevent accidental actuation of such nasal delivery devices. This sturdiness would also need to be balanced with a continued need for ease in operation. It is an object of the present invention to provide such an improved nasal delivery device.

SUMMARY

The present disclosure provides a nasal delivery device with a device body that includes a trigger end and an outlet end. The nasal delivery device also includes a trigger assembly coupled to the trigger end of the device body, a drug container supported by the device body, and a spring-loaded activator assembly supported by the device body and disposed between the trigger assembly and the drug container.

In one embodiment, the nasal delivery device has a device body including a trigger end and an outlet end; a trigger assembly coupled to the trigger end of the device body; an output assembly including a drug container supported by the device body and including a medication, a first seal and an outlet seal; and an elastic activator device configured to bias the push rod to open the first seal and to drive movement of the drug container towards the outlet end to open the outlet seal and expel the medication from the outlet end.

In another embodiment, the nasal delivery device has a device body including a trigger end and an outlet end; a trigger assembly coupled to the trigger end of the device body and including at least one prong and a safety rod; an output assembly including a drug container supported by the device body, a first seal and an outlet seal; and an activator assembly including an elastic activator device and at least one latch; and wherein upon activation of the trigger assembly, the at least one prong and the safety rod move towards the outlet end and the safety rod moves clear of the at least one latch and the at least one prong engages the at least one latch to release the elastic activator device.

In yet another embodiment, the nasal delivery device has a device body including a trigger end and an outlet end; a trigger assembly coupled to the trigger end of the device body; a drug container supported by the device body; and an activator assembly operably coupled to the trigger assembly and including a push rod and an elastic activator device, the activator assembly has a series of configurations which include a latched configuration in which the activator assembly is latched relative to the device body and the elastic activator device is loaded; an unlatched configuration in which the activator assembly is released from the device body; and a delivery configuration in which the elastic activator device is axially moved toward the outlet end to drive the push rod into engagement with the drug container thereby moving the drug container towards the outlet end to expel the medication out from the outlet end.

BRIEF DESCRIPTION OF THE DRAWINGS

The above mentioned and other features of this present disclosure, and the manner of attaining them, will become more apparent and the invention itself will be better understood by reference to the following description of embodiments of the present disclosure taken in conjunction with the accompanying drawings, wherein.

Figure 1:
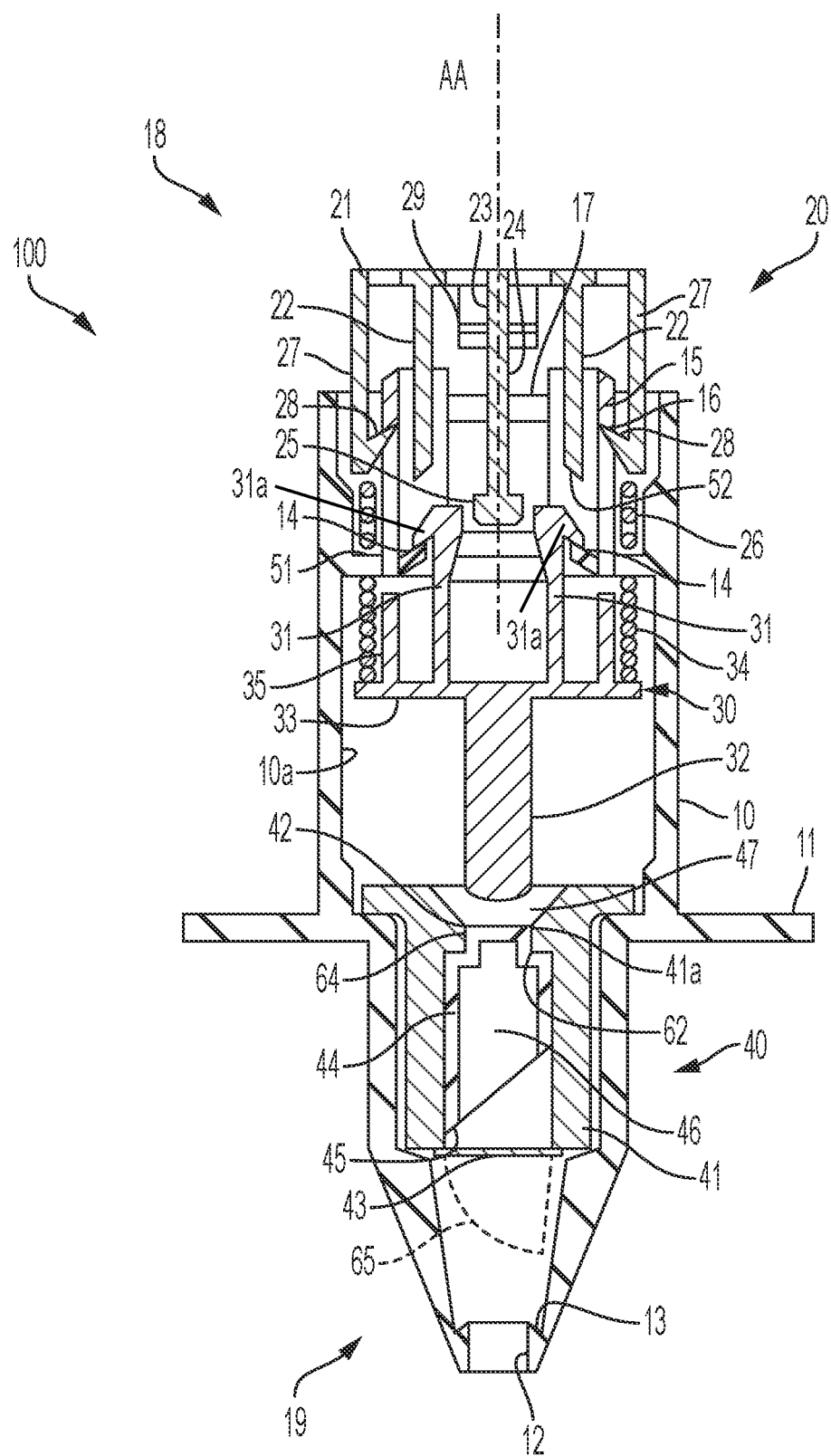
FIG. 1 is a cross-sectional view of an embodiment of the nasal delivery device.

Corresponding reference characters indicate corresponding parts throughout the several views. Although the exemplification set out herein illustrates embodiments of the present disclosure, in several forms, the embodiments disclosed below are not intended to be exhaustive or to be construed as limiting the scope of the invention to the precise forms disclosed.

DETAILED DESCRIPTION

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

The proposed designs are for a nasal delivery device. The designs have advantages such as, for example, the use of two seals in the device instead of four seals found in some devices. Another advantage of some of the embodiments may be reduced actuation force since the dosing energy is supplied by a loaded compression spring. The actuation force will be comparatively low because it is used to release the spring and does not need to provide the energy to expel the drug media. Another advantage of some of the embodiments may be the provision of a lock/safety feature to prevent inadvertent actuation by rough handling or shipping. Another advantage may be a housing snap arrangement to provide a locking feature to maintain the snap fit joint between the nozzle outlet and the device housing. Another advantage of some of the embodiments may be the provision of a drug container with a seal piercing design to allow the dosing spring to push the container through the seal and to expel the drug as the container stops.

FIG. 1 illustrates a first exemplary embodiment of a nasal delivery device 100. As shown in FIG. 1, nasal delivery device 100 includes a device housing or body 10, a trigger assembly 20, an activator assembly 30, and an output assembly 40, each of which is described further below. The components are disposed relative to one another along a common axis AA.

Device body 10 includes a trigger end 18 (which may be referred to herein as an "upper" end based on the orientation of FIG. 1) and an outlet end 19 (which may be referred to herein as a "lower" end based on the orientation of FIG. 1). Other orientational terms such as "vertical", "horizontal", "above", "below", etc. are used based on the orientation of FIG. 1. However, it is understood that the device body 100 can be used in other orientations.

Between the trigger end 18 and the outlet end 19, device body 10 includes a finger grasp 11 configured to be grasped by an operator. Finger grasp 11 may take any number of forms and sizes, and may have a cross-sectional area greater than the cross-sectional area of the device body 10 as shown. For example, finger grasp 11 may be a single circular flange surrounding the entire device body 10, it may be distinct flanges extending outwardly from opposing sides of device body 10, and/or it may be shaped to surround a finger of the operator.

Near the trigger end 18 of device body 10, device body 10 includes one or more internal trigger assembly catches 15. Trigger assembly catches 15 engage with a portion of trigger assembly 20. More specifically, trigger assembly catches 15 each include a radially outward extending lower lip 16 that prevents trigger portion 20 from being detached from nasal delivery device 100, as discussed in greater detail below. Catches in the position shown in the figures can be extensions from an internal wall 10a of the device body as part of the injection molding and/or may be a separate component fixedly secured to the internal of the device body.

Continuing downward from trigger assembly catches 15, device body 10 includes an internal shoulder 51. Internal shoulder 51 may be a single circular shoulder 51 or multiple individual shoulders 51 extending radially inward from the internal wall 10a. The internal shoulder 51 may interact with both the trigger portion 20 on one side and the activator assembly 30 on the other side, as discussed in greater detail below.

Device body 10 also includes an activator catch 14. Activator catch 14 could include a single circular catch 14 or multiple individual catches 14. Activator catch 14 extends radially inward from internal wall 10a of device body 10 and may be angled at least partially axially towards the trigger end 18 of device body 10. The angled orientation of activator catch 14 may allow activator catch 14 to engage with a portion of activator assembly 30 to keep activator assembly 30 in a latched configuration until activator assembly is unlatched. Activator assembly 30 and its various configurations will be discussed in greater detail below.

At the outlet end 19, device body 10 includes a nozzle 12 from which the drug is dispensed. Device body 10 also includes a drug container stop 13 that extends radially inward from device body 10 around the nozzle 12. Stop 13 may be angled at least partially axially towards the trigger end 18 of device body 10. The angled orientation of drug container stop 13 may allow drug container stop 13 to prevent a portion of output assembly 40 from expelling from nasal delivery device 100. The operation of outlet portion 40 of nasal delivery device 100 will be discussed in further detail below.

Returning towards the trigger end 18 of device body 10, a depressed button catch receiver 17 is provided, shown as a notch defined in the device body. Depressed button catch receiver 17 is a depressed portion of device body 10 that receives a portion of trigger assembly 20 when trigger assembly 20 is depressed.

The trigger assembly 20 is coupled to the trigger end 18 of device body 10. Trigger assembly 20 includes a button 21 that extends axially beyond the trigger end 18 of device body 10 for access by the operator. Button 21 defines an upper wall, on which the operator depresses, and a downwardly extending sidewall extending from the upper wall that encloses a button cavity. Button 21 includes at least one trigger assembly latch 27. Latch 27 may be incorporated into the sidewall or may be segmented from the sidewall. In one example, trigger assembly latch 27 extends from the upper wall of button 21 axially into device body 10 toward the outlet end and ends with a radially inward extending lip 28. Trigger assembly latch 27 can include a single continuous lip 28 or a plurality of individual lips 28. Lips 28 of trigger assembly latch 27 engage trigger assembly catches 15 of device body 10 to prevent button 21 from being detached from nasal delivery device 100, as noted above.

Button 21 also includes prongs 22. Prongs 22 are located radially inward of and in spaced relationship with trigger assembly latches 27 and extend axially into device body 10 toward the outlet end from the upper wall. Prongs 22 end at their lowest point with angled ends 52. In another example, the prongs 22 may be defined as a single internal cylindrical body extending from the upper wall.

Button 21 may further include a safety rod 23 optionally. Safety rod 23 is located radially inward of and in spaced relationship with both trigger assembly latch 27 and prongs 22. Safety rod 23 extends axially from a central portion of upper wall of button 21 along the axis AA toward the outlet end and into device body 10 axially beyond the latch 27 and prongs 22. In an embodiment, the safety rod 23 has a constant cross-sectional area. In other embodiments, safety rod 23 can include two portions, a first, cross-sectionally narrow portion 24 having a second cross-sectional area W2 (see FIG. 5) and a second, wide portion 25 comparted to the first portion 24 having a larger cross-sectional area W1 (see FIG. 5). As shown in FIG. 1, first portion 24 forms the stem of safety rod 23 and extends axially from button 21 toward the outlet end, while second portion 25 forms an enlarged end of safety rod 23 having a short and wide profile compared to first portion 24. The function of the safety rod 23 will become apparent below.

Trigger assembly 20 also includes an elastic trigger device 26 (e.g., an axially compressible spring) that biases button 21 up and away from device body 10 and from activator assembly 30. In the embodiment of FIG. 1, elastic trigger device 26 surrounds the internal diameter of device body 10 and sits within a cylindrical chamber of device body 10 above internal shoulder 51. Elastic trigger device 26 is shown axially disposed between internal shoulder 51 and the latch 27. Elastic trigger device 26 of the embodiment of FIG. 1 biases button 21 through contact with internal shoulder 51 below and trigger assembly latch 27 above. By the biasing, the button has an initial extended configuration that is defined physically by engagement between lips 28 of trigger assembly latch 27 and trigger assembly catches 15. Button is movable from the extended configuration to a fully depressed configuration when an axial force is applied to the upper wall of the button in an axial direction toward the outlet end that is greater than the biasing force of elastic trigger device 26. When such a great force is applied, the lips 28 of trigger assembly latch 27 disengage from trigger assembly catches 15 as the button travels axially toward the output end relative to the device body.

Activator assembly 30 includes an activator plate 33 positioned interiorly within device body 10 and initially axially spaced from an upper surface 41a of a drug container housing 41 disposed in the device body to allow clearance for movement of the activator assembly within the device housing. Activator assembly 30 also includes a plurality of latches 31 that extend axially towards the trigger end 18 of device body 10 from activator plate 33. The ends 31a of latches 31 engage with activator catch 14 of device body 10 to hold activator assembly 30 in a latched configuration and are configured to flex radially to disengage from the catch 14. Activator assembly may also include an outer wall 35 extending axially toward trigger end and disposed radially outward of and in spaced relationship with latches 31. As shown, outer wall 35 may be spaced radially inward from the outer edge of the activator plate to define a cylindrical chamber for an elastic activator device 34.

Activator assembly 30 also includes elastic activator device 34 (e.g., an axially compressible spring) in contact with the outer edges of activator plate 33, surrounding outer wall 35, and the bottom of internal shoulder 51 of device body 10, shown as axially aligned and opposite with elastic trigger device 26. Elastic activator device 34 biases activator assembly 30 towards the outlet end of device body 10. As shown in FIG. 1, elastic activator device 34 is loaded while activator assembly 30 is in the latched position. The nature and function of elastic activator device 34 will be discussed in greater detail below.

Activator assembly 30 also includes a push rod 32 coupled to a central portion of activator plate 33 and extending axially towards the outlet end 19 of device body 10 along the axis AA. The shape and size of push rod 32 is configured for receipt in output assembly 40. In one example, the push rod 32 and the safety rod 23 are in axial alignment along axis AA. Push rod 32 may have a tapered end.

Output assembly 40 may include a drug container housing 41 that is nested within device body 10 towards the outlet end 19 of device body 10. In one embodiment, the housing 41 is a separate component nested in the device body 10. In another embodiment, the configuration of housing 41 shown in the figures is part of the interior of the device body or integrally formed with the device body. Drug container housing 41 includes a hole 47 defined in an upper end of housing 41 that is closest to the trigger end 18 of device body 10 that may match the shape and size of push rod 32. Hole 47 may be funnel shaped, having a wider upper end and a narrower lower end to help guide the end of push rod 32 to the upper end of the drug container 44. Nested within drug container housing 41 is drug container 44. Drug container 44 encloses a drug chamber 46 which contains a medication in powder or fluid form, such as, for example, insulin for treatment of diabetes, glucagon to prevent severe hypoglycemia, dihydroergotamine (DHE) for treatment of migraine, growth hormones, etc. Drug container housing 41 also defines a first seal 42 in that it physically cooperates with drug container 44 preventing anything from entering drug container housing 41 through the hole 47 of drug container housing 41 and/or the drug container 44. The first seal 42 may also retain the drug container 44 in a friction-fit arrangement with the drug container housing 41 or with the device body 10 (not shown) similar to an interior shaped like housing 41. The drug container housing 41 includes an inner sealing portion 62, for example, an inner radial surface of a diametric reduced neck region of housing 41, contiguous with the lower end of the hole 47, that is sized and shaped to sealably engage a portion 64 of the drug container 44. For example, such portion 64 may be defined by an outer radial surface of a diametric head end. Portion 62 and portion 64 engage one another radially define the first seal 42 via an interference fit. Drug container housing 41 also includes an outlet seal 43 lining the bottom of drug container 44 as an axial end seal and preventing drug leakage and contamination from the outside environment. Outlet seal 43 can be a film such as foil seal, or any other sealant film material commonly used or known in the medical device field. Drug container housing 41 also contains a piercing portion 45 that is shaped and configured to pierce through or otherwise open the outlet seal 43. Piercing portion 45 is shown as a tapered end of the drug container 44 where a portion of the wall extends further than another portion of the wall. The end of the piercing portion 45 is shown spaced from the outlet seal 43 pre-seal where the medication can be disposed between the outlet seal and up into the drug container 44. When the drug container 44 slides along the inner wall of the drug container housing 41, the end of piercing portion 45 is physically stopped by drug container stop 13, which is shown as an annular recess defined along the inner wall 10a in close proximity to nozzle 12. The dashed lines 65 is representative of the location of the outlet seal 43 after being pierced.

FIGS. 2-5 depict several different configurations of nasal delivery device 100 and show various stages in the use of device 100.

Figure 2:
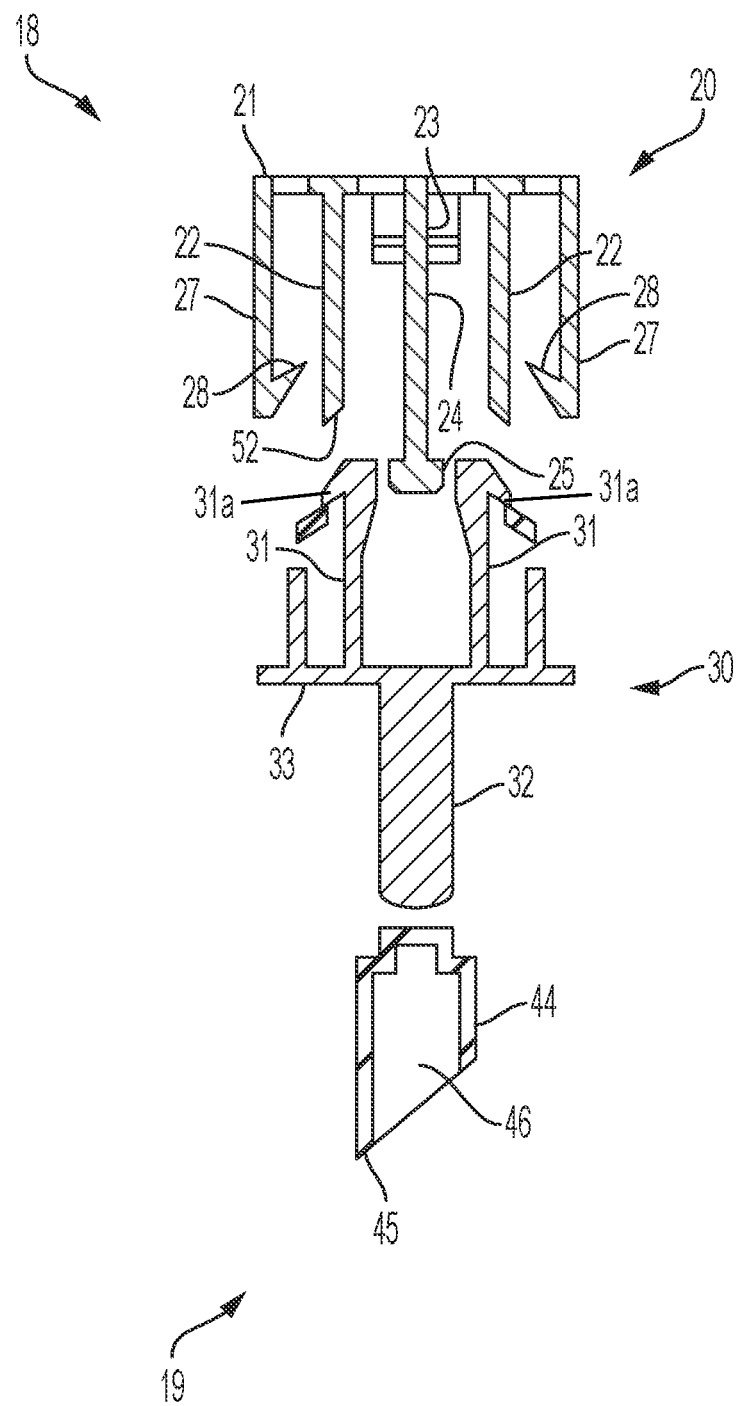
FIG. 2 is a partial cross-sectional view of the nasal delivery device of FIG. 1 in a latched configuration.

FIG. 2 shows nasal delivery device 100 in a latched configuration. In the latched configuration, trigger assembly 20 has an inactive configuration. Button 21 is biased in the extended configuration towards trigger end 18 of device body 10 by elastic trigger device 26. Trigger assembly latches 27 are engaged with lip 16 of trigger assembly catch 15 and prevent button 21 from being removed from nasal delivery device 100. Prongs 22 are axially spaced apart from latches 31 of activator assembly 30. Also, latches 31 are engaged and latched onto activator catch 14 such that activator 30 is held up against the load of elastic activator device 34. Safety rod 23 is in a raised position in the latched configuration, where second portion 25 of safety rod 23 is positioned radially between ends 31a of latches 31 of activator assembly 30. In this raised position, second portion 25 of safety rod 23 inhibits the radial inward movement of ends 31a of latches 31 to prevent latches 31 from moving enough to disengage or unlatch from activator catch 14 in the event of accidental activation of activator assembly 30, such as an accidental drop or other shock load.

Figure 3:
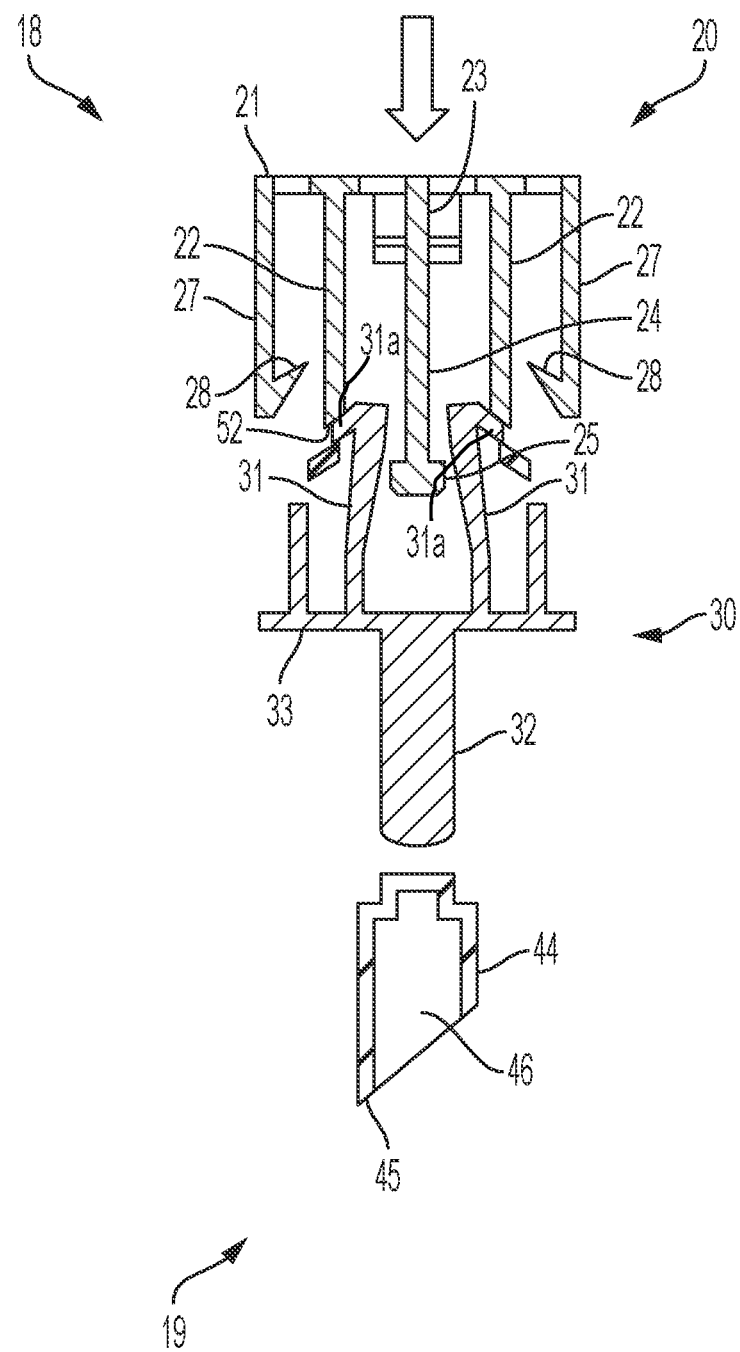
FIG. 3 is a partial cross-sectional view of the nasal delivery device of FIG. 1 in an intermediate configuration.

FIG. 3 shows nasal delivery device 100 in an intermediate configuration. In the intermediate configuration, button 21 is depressed slightly and trigger assembly 20 moves down against the bias of elastic trigger device 26 toward its fully depressed configuration from its extended configuration. Trigger assembly latches 27 disengage from trigger assembly catch 15 (FIG. 1). Prongs 22 begin to approach the ends 31a of latches 31 of activator assembly 30. Due to the shape and angle of both prongs 22 and latch ends 31a, as prongs 22 move down and slidably engage latch ends 31a, prongs 22 push ends 31a of latches 31 radially inward and toward safety rod 23. In the intermediate position, button 21 has not been depressed enough or is not at an axial position sufficient for unlatching, and second portion 25 of safety rod 23 still interferes with ends 31a of latches 31 and prevents latches 31 from completely unlatching from activator catch 14.

Figure 4:
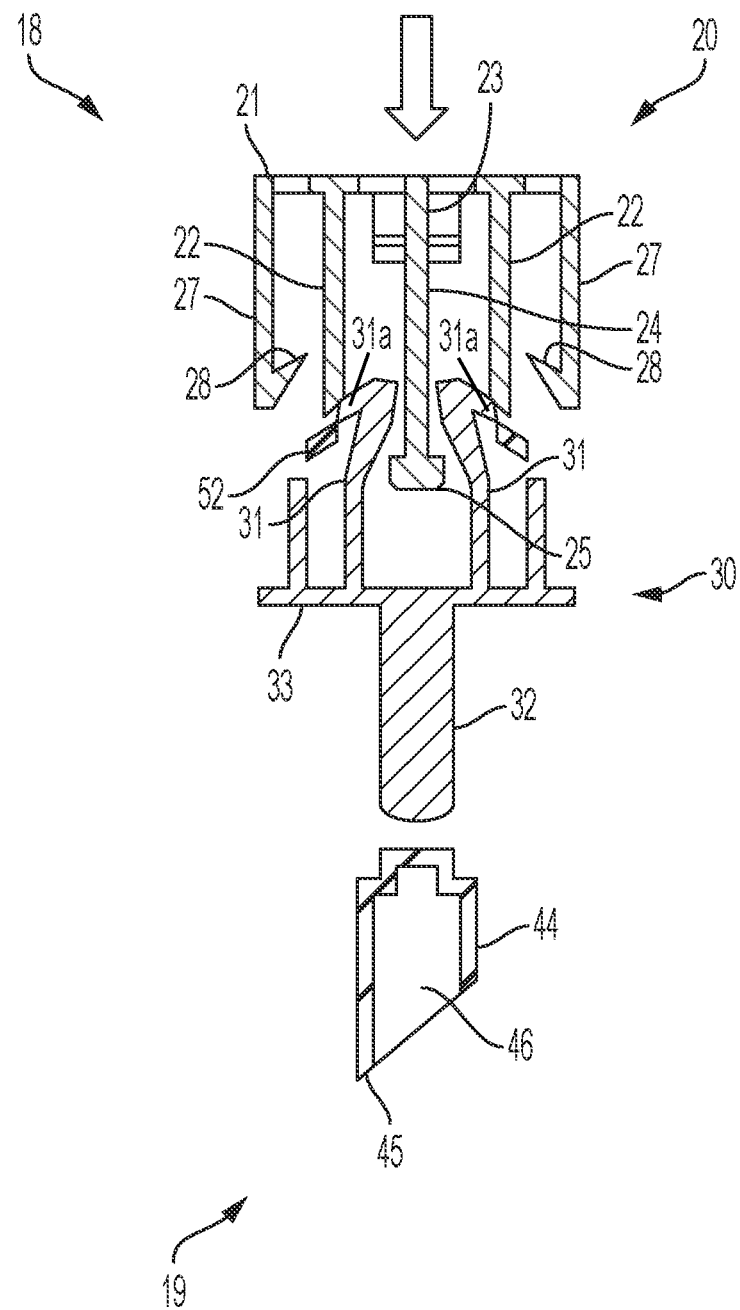
FIG. 4 is a partial cross-sectional view of the nasal delivery device of FIG. 1 in an unlatched configuration.

FIG. 4 shows nasal delivery device 100 in an unlatched configuration in the moment before the stored energy in the compressed elastic activator device 34 (FIG. 1) pushes activator assembly 30 down towards the outlet end 19. In the unlatched configuration, button 21 has been moved to its fully depressed configuration towards the outlet end 19 of device body 10. Fully depressing button 21 moves the wide, second portion 25 of safety rod 23 axially relative to latches 31 toward the outlet end to a clearance position as shown in FIG. 4 and moves the narrow, first portion 24 of safety rod 23 radially between ends 31a of latches 31. Fully depressing button 21 also causes prongs 22 to contact activator catch 14 while pushing ends 31a of latches 31 radially inward away from activator catch 14. Without interference from safety rod 23, latches 31 are released radially from activator catch 14 to allow the preloaded elastic activator device to unload for axially driving the activator plate.

Figure 5:
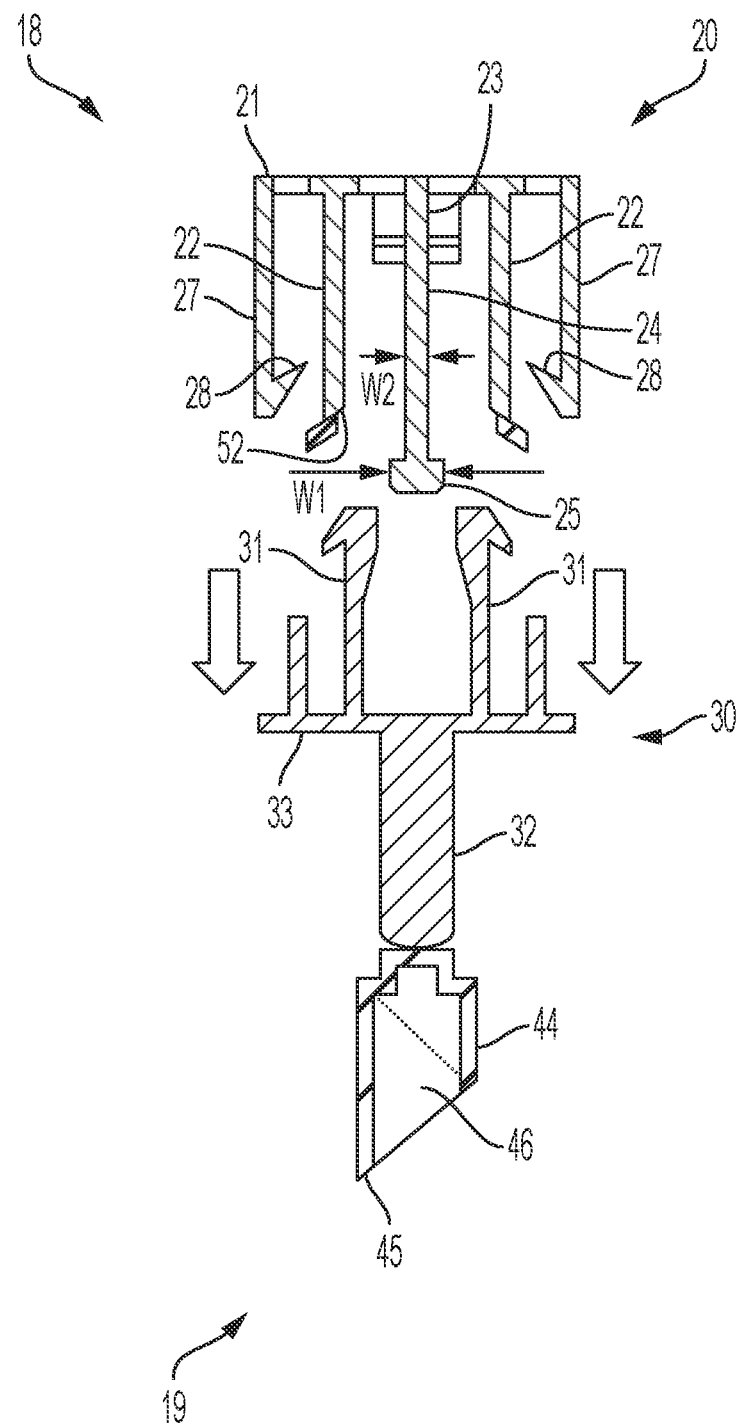
FIG. 5 is a partial cross-sectional view of the nasal delivery device of FIG. 1 in a delivery configuration.

FIG. 5 shows nasal delivery device 100 in a delivery configuration. In this delivery configuration, the preloaded elastic activator device 34 (FIG. 1) has unloaded its energy and applied an axial force on activator plate 33 of activator assembly 30 in the direction of the outlet end, which has pushed activator assembly 30 towards the outlet end 19 of device body 10. As activator assembly 30 moves towards the outlet end 19 of device body 10, push rod 32 enters the hole 47 of drug container housing 41. As push rod 32 pushes into the head end of the drug container 44, push rod 32 with sufficient axial force breaks the radial friction force of first seal 42 which allows drug container 44 to be loosened from drug container housing 41. Push rod 32 continues to push axially toward the outlet end and apply an axial force on drug container 44 towards the outlet end 19 of device body 10. As drug container 44 is pushed axially, piercing portion 45 on drug container 44 slices through outlet seal 43 of drug container housing 41. Drug container 44 stops moving axially upon contacting the drug container stop 13. However, because the outlet seal 43 of drug container 44 has been broken, the drug powder in drug chamber 46 continues to travel axially through the broken outlet seal 43, through nozzle 12, and toward the patient. The ability to deliver the drug using the energy of the elastic activator device 34 (FIG. 1) that is converted to momentum in the medication to expel the medication from the outlet may avoid the need for compressed air inside the nasal delivery device 100.

Nasal delivery device 100 is a single use drug delivery device. In order to determine whether a specific assembly of nasal delivery device 100 has been used or not, trigger assembly 20 stays in the depressed position after depression of trigger assembly 20 and activation of activator assembly 30. In the embodiment of FIG. 1, as button 21 of trigger assembly 20 is depressed, depressed button catch 29 engages with depressed button catch receiver 17 of device body 10. Upon complete depression of button 21, depressed button catch 29 and depressed button catch receiver 17 lock together in a snap-fit configuration preventing elastic trigger device 26 from resetting the position of trigger assembly 20.

Figure 6:
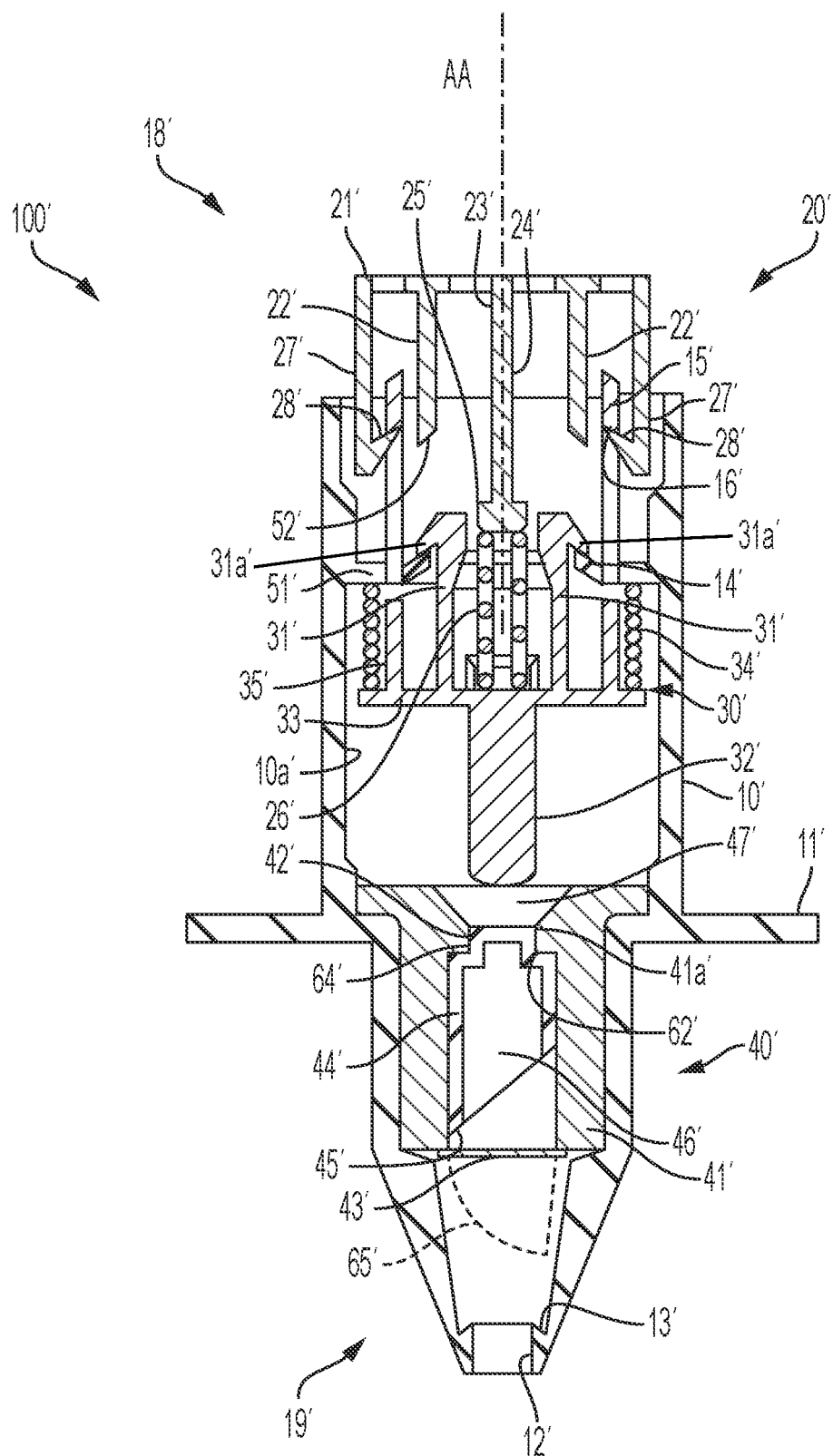
FIG. 6 is a cross-sectional view of another embodiment of the nasal delivery device.

FIG. 6 illustrates a second exemplary embodiment of a nasal delivery device 100'. The second nasal delivery device 100' of FIG. 6 is similar to the first nasal delivery device 100 of FIG. 1, with like reference numerals indicating like elements, except as described below. The second nasal delivery device 100' includes an elastic trigger device 26' similar to elastic trigger device 26. However, elastic trigger device 26 is shown located beneath trigger assembly latches 27' and axially spaced from elastic activation trigger toward the trigger end as shown in FIG. 1, the elastic trigger device 26' of FIG. 6 is a narrow spring located between an end portion 25' of safety rod 23' and activator plate 33' of activator assembly 30'. The elastic trigger device 26' is shown disposed radially inward of the elastic activation trigger 34' in a coaxial relationship. The elastic trigger device 26' is shown disposed radially inward of latches 31' in a coaxial relationship. Also, as button 21' of trigger assembly 20' is depressed, trigger assembly latches 27' frictionally engage with the inner wall of device body 10'. The frictional force applied between the inner wall of device body 10' and trigger assembly latches 27' is great enough to retain the button 21 in body 10'. The operation of the device 100' is similar to what is described related to device 100 in FIGS. 2-5. One advantage of the configuration of device 100' may be that elastic trigger device 26' may contribute as an additional axial force activation source for trigger 34', in addition to force provided by the elastic activation trigger 34'. To this end, as the button is depressed fully, the elastic trigger device 26' is at least partially loaded as it is axially compressed, and when in the unlatched configuration, the stored energy in the elastic trigger device 26' is applied directly to the activation plate 33' to potentially create greater momentum in the medication to expel the medication from the outlet as a higher rate than in device 100.

While embodiments of the invention have been described as having exemplary designs, the embodiments of the present disclosure may be further modified within the spirit and scope of this disclosure. This application is therefore intended to cover any variations, uses, or adaptations of the disclosed embodiments using its general principles.

Various aspects are described in this disclosure, which include, but are not limited to, the following aspects:

1. A nasal delivery device including: a device body including a trigger end and an outlet end; a trigger assembly coupled to the trigger end of the device body; an output assembly including a drug container supported by the device body and including a medication, a first seal and an outlet seal; and an activator assembly operably coupled to the trigger assembly and including: a push rod which extends towards the drug container, and an elastic activator device configured to bias the push rod to open the first seal and to drive movement of the drug container towards the outlet end to open the outlet seal and expel medication from the outlet end.

2. The nasal delivery device of aspect 1, wherein the trigger assembly further includes an elastic trigger device contacting a portion of the trigger assembly and configured to bias the trigger assembly in a direction opposite the outlet end of the device body.

3. The nasal delivery device of any one of aspects 1-2, wherein the device body includes at least one finger grasp extending laterally from the device body on all sides.

4. The nasal delivery device of any one of aspects 1-3, wherein the output assembly includes a drug container housing configured to support the drug container, the drug container including a piercing portion configured to pierce the outlet seal of the drug container as it moves towards the outlet end.

5. The nasal delivery device of any one of aspects 1-4; wherein the trigger assembly includes prongs extending axially from the trigger assembly toward the outlet end; wherein the activator assembly further includes a plurality of latches extending axially away from the outlet end from the activator assembly; wherein the device body further includes at least one activator catch, extending towards the trigger end at an angle and configured to support the plurality of latches of the activator assembly in the latched configuration; and wherein, in response to the movement of the trigger assembly relative to the device body, the prongs engage the plurality of latches of the activator assembly to release the plurality of latches of the activator assembly from the at least one activator catch of the device body and transition the activator assembly from a latched configuration to an unlatched configuration to permit the elastic activator device to drive the activator assembly axially towards the first seal, wherein the first seal is defined by a radial friction fit between a portion of the drug container and the device body or a drug container housing.

6. The nasal delivery device of aspect 5, wherein the trigger assembly further includes a safety rod extending axially from the trigger assembly toward the outlet end, the safety rod having a first portion with a first cross-sectional area and a second portion with a second cross-sectional area that is smaller than the first cross-sectional area, wherein the first portion is disposed radially between the plurality of latches to inhibit radial movement of the lathes when the activator assembly is in the latched configuration.

7. The nasal delivery device of aspect 6, wherein as the trigger assembly is activated, the safety rod and the prongs move axially toward the outlet end to move the first portion to a clearance position to allow radial movement of the latches toward the second portion and permit unlatching from the at least one activator catch.

8. The nasal delivery device of any one of aspects 1-7, wherein the trigger assembly further includes a plurality of trigger assembly latches extending axially toward the outlet end from the trigger assembly and having a lip at a first end, and the device body includes at least one trigger assembly catch at the trigger end of the device body in engagement with the lip of the plurality of trigger assembly latches when the nasal delivery device is in an un-activated configuration and preventing removal of the trigger assembly.

9. The nasal delivery device of any one of aspects 2-8, wherein the activator assembly includes an activator plate, wherein the elastic activator device is disposed between the activator plate and the device body, and the elastic trigger device is disposed axially between the pushrod and the activator plate.

10. The nasal delivery device of any one of aspects 2-8, wherein the activator assembly includes an activator plate, wherein the elastic activator device is disposed between the activator plate and the device body, and the elastic trigger device is disposed between said portion of the trigger assembly and the device body and axially spaced from the elastic activator device.

11. A nasal delivery device including: a device body including a trigger end and an outlet end; a trigger assembly coupled to the trigger end of the device body and including at least one prong and a safety rod each extending axially toward the outlet end and fixed relative to one another; an output assembly including a drug container supported by the device body, a first seal and an outlet seal; and an activator assembly including an elastic activator device and at least one latch; and wherein upon activation of the trigger assembly, movement of the at least one prong and the safety rod towards the outlet end to position a portion of the safety rod that allows movement of the at least one latch, and the at least one prong engages the at least one latch to release the elastic activator device.

12. The nasal delivery device of aspect 11, wherein the activator assembly further includes a push rod extending axially towards the drug container.

13. The nasal delivery device of aspect 12, wherein the elastic activator device is configured to bias the push rod to open the first seal and to drive axial movement of the drug container towards the outlet end.

14. The nasal delivery device of any one of aspects 11-13, wherein the safety rod of the trigger assembly includes a first portion with a first width and a second portion with a second width that is smaller than the first width, the first portion being disposable radially between ends of the plurality of latches to inhibit release of the elastic activator device.

15. The nasal delivery device of any one of aspects 14, wherein as the trigger assembly is activated, the safety rod and the prongs move axially toward the outlet end, wherein the prongs are in engagement with the ends of the latches and the first portion is cleared from the ends of the latches to allow the latches to move radially inward unlatch by the prongs.

16. The nasal delivery device of any one of aspects 11-13, wherein upon depression of the trigger assembly, the trigger assembly remains depressed.

17. The nasal delivery device of aspect 16, wherein the device body further includes a depressed button catch receiver; the trigger assembly further includes a depressed button catch; and wherein upon depression of the trigger assembly, the depressed button catch engaged the depressed button catch receiver in a snap-fit configuration.

18. A nasal delivery device including: a device body including a trigger end and an outlet end; a trigger assembly coupled to the trigger end of the device body; a drug container supported by the device body and including a medication; and an activator assembly operably coupled to the trigger assembly and including a push rod and an elastic activator device, the activator assembly having: a latched configuration in which the activator assembly is latched relative to the device body and the elastic activator device is loaded; an unlatched configuration in which the activator assembly is released from the device body; and a delivery configuration in which the elastic activator device is axially moved toward the outlet end to drive the push rod into engagement with the drug container thereby moving the drug container towards the outlet end to expel the medication out from the outlet end.

19. The nasal delivery device of aspect 18, wherein: in the latched configuration, the drug container is sealed by a first seal and an outlet seal, wherein the first seal is defined by a radial friction fit between a portion of the drug container and the device body or a drug container housing, and the outlet seal includes a film coupled to the drug container; and in the delivery configuration, the push rod applies an axial force against the drug container to axially move the drug container to open the first seal, and a portion of the drug container after moving engages the film to open the outlet seal, thereby allowing the medication to expel from the drug container.

20. The nasal delivery device of any one of aspects 18-19, wherein: in the latched configuration, the trigger assembly is biased away from the device body; in the delivery configuration, the trigger assembly is fully depressed toward the device body; the activator assembly further including an intermediate configuration in which the trigger assembly is partially depressed between the latched and delivery configurations.

What is claimed is:

1. A nasal delivery device comprising:
a device body including a trigger end and an outlet end;
a trigger assembly coupled to the trigger end of the device body, the trigger assembly including prongs extending axially from the trigger assembly toward the outlet end, and a safety rod extending axially from the trigger assembly toward the outlet end;
an output assembly including a drug container supported by the device body and configured to hold a medication, a first seal and an outlet seal; and
an activator assembly operably coupled to the trigger assembly and including:
a push rod which extends towards the drug container,
a plurality of latches extending axially away from the outlet end from the activator assembly, and
an elastic activator device configured to bias the push rod to open the first seal and to drive movement of the drug container towards the outlet end to open the outlet seal and to expel the medication from the outlet end,
wherein the device body further includes at least one activator catch, extending towards the trigger end at an angle and configured to support the plurality of latches of the activator assembly in the latched configuration; and wherein, in response to the movement of the trigger assembly relative to the device body, the prongs are configured to engage the plurality of latches of the activator assembly to release the plurality of latches of the activator assembly from the at least one activator catch of the device body and transition the activator assembly from a latched configuration to an unlatched configuration to permit the elastic activator device to drive the activator assembly axially towards the first seal, wherein the first seal is defined by a radial friction fit between a portion of the drug container and the device body or a drug container housing, wherein the safety rod has a first portion with a first cross-sectional area and a second portion with a second cross-sectional area that is smaller than the first cross-sectional area, wherein the first portion is disposed radially between the plurality of latches to inhibit radial movement of the latches when the activator assembly is in the latched configuration.

2. The nasal delivery device of claim 1, wherein the trigger assembly further includes an elastic trigger device contacting a portion of the trigger assembly and configured to bias the trigger assembly in a direction opposite the outlet end of the device body.

3. The nasal delivery device of claim 2, wherein the activator assembly includes an activator plate, wherein the elastic activator device is disposed between the activator plate and the device body, and the elastic trigger device is disposed axially between the pushrod and the activator plate.

4. The nasal delivery device of claim 2, wherein the activator assembly includes an activator plate, wherein the elastic activator device is disposed between the activator plate and the device body, and the elastic trigger device is disposed between said portion of the trigger assembly and the device body and axially spaced from the elastic activator device.

5. The nasal delivery device of claim 1, wherein the device body includes at least one finger grasp extending laterally from the device body on all sides.

6. The nasal delivery device of claim 1, wherein the output assembly includes a drug container housing configured to support the drug container, the drug container including a piercing portion configured to pierce the outlet seal of the drug container as it moves towards the outlet end.

7. The nasal delivery device of claim 1, wherein as the trigger assembly is activated, the safety rod and the prongs are configured to move axially toward the outlet end to move the first portion to a clearance position to allow radial movement of the latches toward the second portion and permit unlatching from the at least one activator catch.

8. The nasal delivery device of claim 1, wherein the trigger assembly further includes a plurality of trigger assembly latches extending axially toward the outlet end from the trigger assembly and having a lip at a first end, and the device body includes at least one trigger assembly catch at the trigger end of the device body in engagement with the lip of the plurality of trigger assembly latches when the nasal delivery device is in an un-activated configuration and preventing removal of the trigger assembly.

9. The nasal delivery device of claim 1, wherein the drug container includes the medication contained therein.

* * * * *